(12) United States Patent
Romari et al.

(10) Patent No.: US 9,580,730 B2
(45) Date of Patent: *Feb. 28, 2017

(54) **PRODUCTION OF DOCOSAHEXAENOIC ACID AND/OR EICOSAPENTAENOIC ACID AND/OR CAROTENOIDS IN MIXOTROPHIC MODE BY *NITZSCHIA***

(71) Applicants: Khadidja Romari, Clermont-ferrand (FR); Francois Godart, Genissac (FR); Pierre Calleja, Bordeaux (FR)

(72) Inventors: Khadidja Romari, Clermont-ferrand (FR); Francois Godart, Genissac (FR); Pierre Calleja, Bordeaux (FR)

(73) Assignee: FERMENTALG, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/385,502

(22) PCT Filed: Mar. 15, 2013

(86) PCT No.: PCT/FR2013/050542
§ 371 (c)(1),
(2) Date: Sep. 16, 2014

(87) PCT Pub. No.: WO2013/136025
PCT Pub. Date: Sep. 19, 2013

(65) Prior Publication Data
US 2015/0044737 A1    Feb. 12, 2015

(30) Foreign Application Priority Data

Mar. 16, 2012 (FR) .................................... 12 52378
Aug. 16, 2012 (FR) .................................... 12 57843

(51) Int. Cl.
| | |
|---|---|
| C12P 7/64 | (2006.01) |
| C12R 1/89 | (2006.01) |
| C12P 23/00 | (2006.01) |
| C12N 1/12 | (2006.01) |
| C12N 13/00 | (2006.01) |

(52) U.S. Cl.
CPC .............. *C12P 7/6427* (2013.01); *C12N 1/12* (2013.01); *C12N 13/00* (2013.01); *C12P 7/6472* (2013.01); *C12P 23/00* (2013.01); *C12R 1/89* (2013.01)

(58) Field of Classification Search
CPC ........ A23L 1/19; C12P 7/6427; C12P 7/6472; C12N 13/00; C12R 1/89
See application file for complete search history.

(56) References Cited

U.S. PATENT DOCUMENTS

| | | | | |
|---|---|---|---|---|
| 3,316,674 | A * | 5/1967 | Shirota ................. | A01G 33/00 435/257.3 |
| 3,444,647 | A * | 5/1969 | Takahashi ............. | A01G 33/00 210/602 |
| 5,381,075 | A * | 1/1995 | Jordan .................. | C12M 21/02 307/115 |
| 2006/0166343 | A1* | 7/2006 | Hankamer ............ | C12N 1/12 435/168 |
| 2009/0305942 | A1* | 12/2009 | Day ..................... | C12P 7/6418 510/437 |

FOREIGN PATENT DOCUMENTS

| | | |
|---|---|---|
| WO | 96/21723 A1 | 7/1996 |
| WO | 2009/134114 A1 | 11/2009 |

OTHER PUBLICATIONS

U.S. Appl. No. 13/822,805; U.S. Appl. No. 13/878,468; U.S. Appl. No. 14/124,367; U.S. Appl. No. 14/127,389; U.S. Appl. No. 14/124,829; U.S. Appl. No. 14/385,305; U.S. Appl. No. 14/385,502; U.S. Appl. No. 14/385,507.*
International Search Report, dated Jul. 2, 2013, from corresponding PCT application.
Wan-Loy Chu et al., "Environmental effects on growth and biochemical composition of Nitzschia inconspicua Grunow", Journal of Applied Physology, 1996, pp. 389-396, vol. 8, No. 4-5.
Zhi-You Wen et al., "Production potential of eicosapentaenoic acid by the diatom Nitzschia laevis", Biotechnology Letters, May 1, 2000, pp. 727-733, vol. 22, No. 9.
Ceron Garcia et al., "Mixotrophic production of marine microalga *Phaeodactylum tricornutum* on various carbon sources", Journal of Microbiology and Biotechnology, May 2006, pp. 689-694, vol. 16, No. 5.
Frank Pennington et al., "Carotenoid Distribution Patterns in Bacillariophyceae (Diatoms)", Biochemical Systematics and Ecology, Dec. 14, 1988, pp. 589-592, vol. 16, No. 7-8.

\* cited by examiner

*Primary Examiner* — Ruth Davis
(74) *Attorney, Agent, or Firm* — Young & Thompson

(57) ABSTRACT

New strains of microalgae belonging to the *Nitzschia* genus, allow high-yield production of lipids, in particular of docosahexaenoic acid (DHA) and/or eicosapentaenoic acid (EPA) and/or carotenoids, in particular fucoxanthin, in mixotrophic mode, and a method for selecting and culturing such strains, using a variable and/or discontinuous light source, in particular a flashing light.

9 Claims, No Drawings

PRODUCTION OF DOCOSAHEXAENOIC ACID AND/OR EICOSAPENTAENOIC ACID AND/OR CAROTENOIDS IN MIXOTROPHIC MODE BY *NITZSCHIA*

The invention relates to a method of culture in mixotrophic mode, in particular in the presence of discontinuous and/or variable illumination with light, of a microalga of the genus *Nitzschia*, in particular of the species *Nitzschia brevirostris*. The method makes it possible to obtain a high yield of biomass and enrichment of the thus cultured microalgae in lipids and more particularly in docosahexanoic acid (DHA) and/or eicosapentaenoic acid (EPA). The method also makes it possible to obtain an enrichment in carotenoids of the thus cultured microalgae, and more particularly, in fucoxanthin. The method thus makes it possible to select strains of *Nitzschia*, in particular of *Nitzschia brevirostris*, with mixotrophic character, and having a high yield of lipids and more particularly of polyunsaturated fatty acids, and/or a high yield of carotenoids, more particularly fucoxanthin. The invention also relates to a novel strain of microalga belonging to the species *Nitzschia brevirostris*, particularly suitable for the production of carotenoids. This novel strain of *Nitzschia brevirostris* is useful for producing docosahexaenoic acid (DHA) and/or eicosapentaenoic acid (EPA) and/or fucoxanthin in mixotrophic mode.

Preamble

Microalgae are autotrophic photosynthetic microorganisms, i.e. they have the ability to grow autonomously by photosynthesis.

Microalgae develop both in the marine aquatic media and in fresh or brackish waters, as well as in various land habitats.

Most species of the microalgae found in fresh water or in the oceans are generally autotrophic, i.e. they can only grow by photosynthesis. For these species, the presence in their environment of organic carbon-containing substrates or organic matter is not favourable to them, and does not improve their growth. However, a certain number of species of microalgae, of very varied families and origins, are found to be not strictly autotrophic. Thus, some of them, said to be heterotrophic, are capable of developing in the total absence of light, by fermentation, i.e. by using organic matter.

Other species of microalgae, for which photosynthesis remains essential for their development, are capable of benefiting both from photosynthesis and from organic matter present in their environment. These intermediate species, said to be mixotrophic, can be cultured in the presence of both light and organic matter.

This particularity of so-called "mixotrophic" algae seems to be related with their metabolism, which allows them to carry out photosynthesis and fermentation simultaneously. Both types of metabolism co-exist with a positive overall effect on the growth of the algae [Yang, C. et al. (2000); *Biochemical Engineering Journal*, 6: 87-102].

Microalgae are currently the subject of numerous industrial projects since some species are capable of accumulating or secreting major quantities of lipids, in particular polyunsaturated fatty acids.

Among these polyunsaturated fatty acids, certain highly unsaturated fatty acids (HUFA) of the omega-3 series (PUFA-ω3), in particular eicosapentaenoic acid (EPA or C20:5 ω3) and docosahexaenoic acid (DHA or C22:6 ω3), and of the omega-6 series (PUFA-ω6), in particular arachidonic acid (ARA or AA or also eicosatetraenoic acid C20:4 ω6) have a recognized nutritional importance, and have strong potential in terms of therapeutic applications.

Regarded as an essential nutrient, DHA is necessary to the normal functional development of cells, and plays a crucial role in various biochemical processes and functions. Its polyunsaturated character confers on it a crucial importance in relation to the properties of the cell membrane, both in plants and in animals: fluidity, flexibility and selective permeability allowing for example efficient adaptation, and even survival, at low temperatures in particular in fish.

DHA is a major structural constituent of the human brain. DHA represents 15-20% of the cerebral cortex (an adult's brain contains at least 20 g of DHA) and 30-60% of the retina. It is essential for the development of the nervous system and for retinal function, by incorporation into the cell membranes, and plays a major role in the acquisition and the satisfactory maintenance of the mechanisms of vision and memory.

Fish oils, from the fishing industry, are currently the main commercial source of these types of fatty acids. However, while these oils find new applications (food supplement in aquaculture, incorporation into margarines), marine halieutic resources are becoming scarce because of intensive fishing activity.

Therefore, new sources of these fatty acids such as EPA, DHA and ARA, have to be sought in order to meet, in the future, the increasing demand for these types of polyunsaturated fatty acids.

In addition to their capability of synthesizing fatty acids de novo, microalgae provide several advantages compared to fish oils: they may be cultured in vitro under controlled conditions, which allows production of a biomass of a relatively constant biochemical composition, and, in addition, unlike fish oils, they do not have an unpleasant odour and their lipids contain little or no cholesterol.

Finally, the lipids produced by microalgae have a simpler fatty acid profile than that of fish oils, which limits the steps for separating the fatty acids of interest.

At present, the classification of algae is still based widely on morphological criteria and on the character of the photosynthetic pigments that their cells contain. Consequently, it is not very indicative of the autotrophic, heterotrophic or mixotrophic character of the algal species, whereas the latter cover a very great diversity of species and forms [Dubinsky et al. (2010); *Hydrobiologia*, 639:153-171].

The taxonomic classification of eukaryotic algae contains 14 phyla. Large variations exist among the species of the different classes making up these phyla that produce fatty acids, as regards the polyunsaturated fatty acid content of the microalgae. Moreover, the relative proportions of lipids, in particular of EPA, DHA and of ARA in the lipid profiles, vary according to the species and the culture conditions.

On the other hand, carotenoids are also molecules of interest. They are generally used as pigments, but they also have an important role for human health as antioxidant agents. Finally, they have the ability to stimulate the immune system. Fucoxanthin is an example of a carotenoid, and is in particular contained in wakame, an alga used in Japanese cuisine.

To implement the production of fatty acids and/or carotenoids by microalgae on an industrial scale, several factors must be taken into account. For example, cultures may be carried out under autotrophic, mixotrophic or heterotrophic conditions depending on the strain, the temperature, the lighting conditions and the size of the fermenters. For example, cultures may also be carried out in 1 L containers, in a laboratory, in photo-bioreactors, and in 100,000 L containers or in open ponds (several hectares). However, the costs of energy and other resources such as manpower and the ease of monitoring the culture must be taken into account for developing ideal culture conditions.

In any case, it is desirable that the microalgae are cultured under optimum conditions for increasing the yield of the fatty acid(s) and/or carotenoid(s) to be produced. Thus, it is preferable to have a yield that is as high as possible (for example biomass above 30 g/l of dry matter, and more than 20% of fatty acids by weight relative to the dry matter). For carotenoids, a yield above 0.2% of microalgal dry matter is desirable.

The microalgae of the genus *Nitzschia* are marine diatoms that are generally found in cold seas such as those of the Arctic or the Antarctic. These microalgae are known mainly for the production of eicosapentaenoic acid (EPA) in heterotrophic mode.

However, it is to be noted that the mixotrophic mode has been studied on the species *Nitzschia laevis* in order to assess its impact on the synthesis of EPA.

Thus, it was after numerous experiments under unusual lighting conditions and with the addition of various substrates that the applicant succeeded in isolating microalgal strains of the species *Nitzschia brevirostris* that can be cultured in mixotrophic mode, allowing, under the conditions of the present invention, a high-yield production of polyunsaturated fatty acids, in particular DHA and/or EPA and/or fucoxanthin.

One strain (FCC 810) representing novel strains of *Nitzschia brevirostris* thus isolated and selected, was deposited at the CCAP (Culture Collection of Algae and Protozoa, Scottish Association for Marine Science, Dunstaffnage Marine Laboratory, Oban, Argyll PA37 1QA, Scotland, United Kingdom) according to the provisions of the Treaty of Budapest, under the accession number CCAP 1052/21.

The method of culture and selection consisted more particularly of culturing the microalgae under mixotrophic conditions, in the presence of variable and/or discontinuous illumination, notably in the form of flashes, with a range of specific variations of light intensity and frequency.

The frequent alternation of illuminated phases and phases of darkness or of lower light intensity, generally perceived as stressful for microalgae, surprisingly, made it possible to obtain a high production of biomass, of lipids and more particularly of polyunsaturated fatty acids, and/or one or more carotenoid(s), in particular fucoxanthin, from the strains of *Nitzschia brevirostris*. The application of such strains according to the invention opens the perspective of industrial production of polyunsaturated fatty acids, in particular of DHA and/or of EPA and/or of fucoxanthin, in fermenters benefiting from a reduced light supply, and should therefore make possible energy savings compared to autotrophic modes of culture.

The different aspects and advantages of the invention are detailed below.

DETAILED DESCRIPTION

The present invention therefore relates to a method of culture of microalgae of the genus *Nitzschia*, in particular of the species *Nitzschia brevirostris*, in mixotrophic mode, under conditions of illumination that is discontinuous and/or variable over time, the illumination having variations in intensity, the amplitude of which is generally comprised between 5 µmol·m$^{-2}$·s$^{-1}$ and 1,000 µmol·m$^{-2}$·s$^{-1}$, preferably between 30 and 400 µmol·m$^{-2}$·s$^{-1}$. These variations may generally take place between 2 and 3,600 times per hour, preferably between 2 and 200 times per hour. The method according to the invention allows an enrichment of the microalgae of the genus *Nitzschia* in polyunsaturated fatty acids, more particularly in DHA and/or EPA, and/or carotenoid(s), more particularly in fucoxanthin.

These culture conditions make it possible to supply a defined quantity of light. This light supply may comprise phases of discontinuous and/or variable illumination, with variations in intensity that may have identical or different amplitudes. The illumination may in particular be in the form of flashes.

The advantage of this method is to increase the yield of biomass obtained from the culture. The other is to enrich the thus cultured microalgae in polyunsaturated fatty acids, more particularly in docosahexaenoic acid (DHA) and/or eicosapentaenoic acid (EPA), and/or carotenoid(s), more particularly in fucoxanthin. This method can also be used for selecting strains of the genus *Nitzschia*, in particular of the species *Nitzschia brevirostris*, with a mixotrophic character, and having a high yield of polyunsaturated fatty acids, in particular of DHA and/or EPA, and/or of carotenoid(s), more particularly of fucoxanthin.

Culture of this microalga in mixotrophic mode is preferably carried out in the presence of 5 mM to 1 M, preferably from 50 mM to 800 mM, more preferentially from 70 mM to 600 mM, and even more preferentially from 100 mM to 500 mM of an organic carbon-containing substrate. The substrate is supplied continually during the culture, so as to allow the cells to accumulate a significant concentration of lipids. Additional substrate is added to the culture medium during the culture process so as to maintain a constant concentration. This organic carbon-containing substrate comprises preferentially, in pure form or as a mixture: glucose, derivatives of cellulose, lactate, lactose, saccharose, acetate and/or glycerol.

The organic carbon-containing substrate contained in the culture medium may consist in complex molecules or in a mixture of substrates. The products resulting from the biotransformation of starch, for example starting from maize, wheat or potato, notably, starch hydrolysates, which constituted of small sized molecules, for example, organic carbon-containing substrates which may be used for mixotrophic culture of the microalgae according to the invention.

This method is more particularly intended for the use of novel strains of microalgae of the genus *Nitzschia* (Division: Bacillariophyta, Order: Bacillariaceae, Family: Bacillariaceae) [ITIS Catalogue of Life, 2010] selected for their mixotrophic character, notably for their capability to be cultured with a light supply greater than 10 µE, in a mineral medium, for example the f medium plus silica enriched in nitrogen [Guillard, R. R. L. (1975). Culture of phytoplankton for feeding marine invertebrates, in *Culture of Marine Invertebrate Animals*, pp 26-60. Smith W. L. and Chanley M. H (Eds.) Plenum Press, New York], to which an organic carbon-containing substrate is added. Preferably, the organic carbon-containing substrate comprises glucose, or lactate, at a concentration that is equivalent to or greater than 5 mM.

These novel strains of *Nitzschia*, more particularly *Nitzschia brevirostris*, may be isolated and selected by the method of selection and culture according to the invention described hereafter.

A representative strain of the *Nitzschia brevirostris* strains according to the invention is the strain FCC 810 isolated by the applicant and deposited with the CCAP, under the accession number CCAP 1052/21. These strains are capable of producing significant quantities of biomass as well as lipids, and more particularly of DHA and/or EPA, when they are cultured in mixotrophic mode with a variable or discontinuous light supply, according to the invention. They are also capable of producing significant quantities of one or more carotenoid(s), more particularly fucoxanthin.

According to the taxonomic analyses carried out, the strain CCAP 1052/21 belongs to the species *Nitzschia brevirostris*. The invention relates to any strain of the species *Nitzschia brevirostris*, capable of growing under mixotrophic culture conditions such as described in the present application, and capable of producing fatty acids, such as DHA. The invention also relates to any strain of microalga of the genus *Nitzschia*, capable of growing under mixotrophic culture conditions such as described in the present application, and capable of producing fatty acids, such as DHA and/or EPA and/or carotenoids, more particularly fucoxanthin.

The isolated strains of *Nitzschia brevirostris* according to the invention make it possible to produce, under mixotrophic conditions, significant quantities of biomass as well as lipids rich in DHA and/or EPA, said DHA and/or EPA being capable of representing more than 20%, more than 25%, or more than 30% of the total lipids contained in the microalgae. Also the isolated strains of *Nitzschia brevirostris* according to the invention make it possible to produce, under mixotrophic conditions, significant quantities of carotenoid(s), more particularly fucoxanthin, capable of representing more than 0.2% of dry matter, more preferentially more than 0.25% of dry matter, of the total microalgal dry matter (which includes the carotenoids content contained in said microalga).

In the present invention, the biomass obtained with the strain FCC 810, isolated by the applicant, from a culture under mixotrophic conditions in the presence of variable and/or discontinuous illumination, notably in the form of flashes, is from 10 to 60%, more generally from 20 to 50%, greater than that of a culture with the same strain carried out in heterotrophic mode. By heterotrophic mode, it is meant culture conditions with an identical culture medium, but without a light supply.

The invention thus relates to a method for culturing microalgae of the genus *Nitzschia*, in particular of the species *Nitzschia brevirostris* in mixotrophic mode, in the presence of an illumination that is variable and/or discontinuous over time, for example, in the form of flashes, notably with a view to producing polyunsaturated fatty acids, such as DHA and/or EPA, and/or one or more carotenoid(s), such as fucoxanthin.

The invention thus relates to a method for selecting strains of the genus *Nitzschia*, in particular of the species *Nitzschia brevirostris*, with a mixotrophic character, and having a high yield of polyunsaturated fatty acids such as DHA and/or EPA, and/or a high yield of one or more carotenoid(s), more particularly of fucoxanthin, in the presence of an illumination that is variable and/or discontinuous over time.

It appeared that variable and/or discontinuous illumination of the cultures, in particular when used in a culture in mixotrophic mode, had a favourable impact on the development of the algae and made it possible to increase the productivity of the latter, in particular with regard to their production of lipids and/or carotenoids. Without being bound to theory, the inventor believes that a discontinuous and/or variable light supply to the microalgae has the effect of causing a "stress" favourable to the growth and to the synthesis of lipids and/or carotenoids. This phenomenon may be partly explained by the fact that, in nature, microalgae tend to accumulate lipids and/or carotenoids reserves, to withstand the constraints of their environment.

By "discontinuous illumination", it is meant an illumination punctuated by periods of darkness. The periods of darkness may be more than a quarter of the time, preferably, half of the time or more, during which the algae are cultured.

According to a preferred aspect of the invention, the illumination is discontinuous and, more preferentially, in the form of flashes. A flash, within the meaning of the invention, is an illumination with light of short duration, i.e. of less than 30 minutes. The duration of the flash may be less than 15 minutes, preferably less than 5 minutes or yet more preferentially less than 1 minute. According to certain embodiments of the invention, the duration of the flash may be less than a second. For example, the duration of the flash may be $1/10$ of a second, or $2/10$ of a second, or $3/10$ of a second, or $4/10$ of a second, or $5/10$ of a second, or $6/10$ of a second, or $7/10$ of a second, or $8/10$ of a second, or $9/10$ of a second. The illumination with light, or the flash, generally lasts longer than 15 seconds. The duration of the flash is generally comprised between 5 seconds and 10 minutes, preferably between 10 seconds and 2 minutes, more preferentially between 20 seconds and 1 minute.

In general, the number of flashes is comprised between about 2 and 3,600 per hour. It may be, for example, comprised between 100 and 3,600 flashes per hour. It may also be comprised between 120 and 3,000, or between 400 and 2,500, or between 600 and 2,000, or between 800 and 1,500 flashes per hour. It may also be comprised between 2 and 200, preferentially between 10 and 150, more preferentially between 15 and 100, and yet more preferentially between 20 and 50 per hour. The flashes may be emitted at regular or irregular time intervals. In the case of emission at regular intervals, the number of flashes per hour then corresponds to a frequency (F) having a time period (T), it being considered that F=1/T. This time period may be comprised between 1 second and 30 minutes, or between 1 second and 36 seconds, or between 1.2 second and 30 seconds, or between 1.44 second and 9 seconds, or between 1.8 second and 6 seconds, or between 2.4 seconds and 4.5 seconds. This frequency may also be comprised between 18 seconds and 30 minutes, preferentially between 24 seconds and 6 minutes, more preferentially between 36 seconds and 4 minutes, and yet more preferentially between 72 seconds and 3 minutes. The number of flashes per hour is selected as a function of the intensity and duration of the flashes (see below). In general, the intensity of the light supplied in the form of flashes is comprised between 5 and 1,000 $\mu mol \cdot m^{-2} \cdot s^{-1}$, preferably between 5 and 500 $\mu mol \cdot m^{-2} \cdot s^{-1}$, or 50 and 400 $\mu mol \cdot m^{-2} \cdot s^{-1}$, and more preferentially between 150 and 300 $\mu mol \cdot m^{-2} \cdot s^{-1}$. By definition, 1 $\mu mol \cdot m^{-2} \cdot s^{-1}$ corresponds to 1 $\mu E\ m^{-2} \cdot s^{-1}$ (Einstein), a unit often used in the literature.

According to a particular embodiment of the invention, the intensity of the light is comprised between 50 and 200 $\mu mol \cdot m^{-2} \cdot s^{-1}$, the frequency of the flashes is comprised between 10 seconds and 60 minutes for a flash duration comprised between 1 second and 1 minute.

According to another embodiment of the invention, the illumination may be variable, which means that the illumination is not interrupted by phases of darkness, but instead the light intensity varies over time. This variation of the light intensity is regular and may be periodic or cyclic. According to the invention, light may also be supplied combining phases of continuous and discontinuous illumination.

According to the invention, regardless of the illumination conditions, the light intensity supplied to the algae in culture, expressed in micromoles of photons per second per square meter ($\mu mol \cdot m^{-2} \cdot s^{-1}$), varies at least once in any one hour. The amplitude of this variation of light intensity is generally between 5 and 1,000, or between 50 and 800, or between 100 and 600 $\mu mol \cdot m^{-2} \cdot s^{-1}$. The intensity of the light may also vary between 5 and 400 $\mu mol \cdot m^{-2} \cdot s^{-1}$. Preferably, the amplitude of the variation of light intensity is between 70 and 300 $\mu mol \cdot m^{-2} \cdot s^{-1}$ and more preferentially between 100 and 200 $\mu mol \cdot m^{-2} \cdot s^{-1}$.

Said light intensity may attain successively, under conditions of variable illumination, for example, the values 50 $pmol \cdot m^{-2} \cdot s^{-1}$ and 100 $\mu mol \cdot m^{-2}$-1, or 5 and 400 $\mu mol \cdot m^{-2}$-1, or 50 and 800 $\mu mol \cdot m^{-2} \cdot s^{-1}$ several times every hour. Said light intensity may attain successively, preferably, the values 50 and 200 $\mu mol \cdot m^{-2} \cdot s^{-1}$. Alternatively, under conditions of discontinuous illumination, said light intensity may attain successively, several times per hour, for example, the values 0 and 50 $\mu mol \cdot m^{-2} \cdot s^{-1}$, the values 0 and 100 $\mu mol \cdot m^{-2} \cdot s^{-1}$ or still more preferentially the values 0 and 200 $\mu mol \cdot m^{-2} \cdot s^{-1}$. It may also attain successively, several times per hour, for example, the values 0 and 300 $\mu mol \cdot m^{-2} \cdot s^{-1}$, the values 0 and 600 $\mu mol \cdot m^{-2} \cdot s^{-1}$, the values 0 and 800 $\mu mol \cdot m^{-2} \cdot s^{-1}$ or also the values 0 and 1,000 $\mu mol \cdot m^{-2} \cdot s^{-1}$.

According to an embodiment of the invention, regardless of the illumination conditions, the intensity of the light supplied to the culture varies as a function of the cell density. The denser the culture becomes, the more intense the light may be. The cell density is the number of cells per ml and it is measured by the techniques known to one skilled in the art.

At the initial stage of the culture, when the cell density is between about $10^5$ and $5 \times 10^5$ cells per ml, the light intensity may be between 5 and 15 $\mu mol \cdot m^{-2} \cdot s^{-1}$, preferably between 5 and 10 $\mu mol \cdot m^{-2} \cdot s^{-1}$. When the culture reaches a density between $10^6$ and $10^7$ cells per ml, the light intensity may be increased to between 15 and 200 $\mu mol \cdot m^{-2} \cdot s^{-1}$, for example, preferably, between 20 and 50 $\mu mol \cdot m^{-2} \cdot s^{-1}$. When the culture, at the final stage, reaches a density between $10^7$ and $10^8$ cells per ml, the light intensity may be increased to between 50 and 400 $\mu mol \cdot m^{-2} \cdot s^{-1}$ for example, preferably, between 50 and 150 $\mu mol \cdot m^{-2} \cdot s^{-1}$.

According to certain embodiments, for example, when the duration of the flashes is for example less than a minute, or less than a second, the intensity of the light may be higher than the values stated above. At the initial stage of the culture, when the cell density is between about $10^5$ and $5 \times 10^5$ cells per ml, the light intensity may be between 5 and 200 $\mu mol \cdot m^{-2} \cdot s^{-1}$, preferably between 5 and 100 $\mu mol \cdot m^{-2} \cdot s^{-1}$. When the culture reaches a density between $10^6$ and $10^7$ cells per ml, the light intensity may be increased to between 30 and 500 $\mu mol \cdot m^{-2} \cdot s^{-1}$, for example, preferably, between 50 and 400 $\mu mol \cdot m^{-2} \cdot s^{-1}$. When the culture, at the final stage, reaches a density between $10^7$ and $10^8$ cells per ml, the light intensity may be increased to between 100 and 1,000 $\mu mol \cdot m^{-2} \cdot s^{-1}$ for example, preferably between 200 and 500 $\mu mol \cdot m^{-2} \cdot s^{-1}$.

According to an embodiment of the invention, the quantity of light supplied to the culture per hour remains between certain values. It is comprised between about 2,000 and 600,000, preferably between 2,000 and 300,000 $\mu mol \cdot m^{-2}$. It may be comprised between 4,000 and 200,000 $\mu mol \cdot m^{-2}$, per hour.

According to an embodiment of the invention, the culture is illuminated with 30 flashes per hour, each flash having a duration of 30 seconds and an intensity of 10 $\mu mol \cdot m^{-2} \cdot s^{-1}$. The latter gives a total supply of light per hour of 9,000 $\mu mol \cdot m^{-2}$. According to another embodiment of the invention, the culture is illuminated with 20 flashes per hour, each flash having a duration of 30 seconds and an intensity of 20 $\mu mol \cdot m^{-2} \cdot s^{-1}$. The latter gives a total supply of light per hour of 12,000 $\mu mol \cdot m^{-2}$. According to another embodiment of the invention, the culture is illuminated with 45 flashes per hour, each flash having a duration of 15 seconds and an intensity of 5 $\mu mol \cdot m^{-2} \cdot s^{-1}$, which gives a total supply of light per hour of 3,375 $\mu mol \cdot m^{-2}$.

According to another embodiment of the invention, the culture is illuminated with 120 flashes per hour, each flash having a duration of 10 seconds and an intensity of 200 $\mu mol \cdot m^{-2} \cdot s^{-1}$, which gives a total supply of light per hour of 240,000 $\mu mol \cdot m^{-2}$.

As described for the light intensity above, and according to an embodiment of the invention, the quantity of light supplied to the culture per hour may vary as a function of the cell density. At the initial stage of the culture, when the cell density is $10^5$ and $5 \times 10^5$ cells per ml, the total supply of light per hour is generally comprised between about 1,500 and 8,000, preferably 1,500 and 6,000 $\mu mol \cdot m^{-2}$, yet more preferably between 2,000 and 5,000 $\mu mol \cdot m^{-2}$. When the culture reaches a density between $10^6$ and $10^7$ cells per ml, the total supply of light per hour may be increased until between 6,000 and 67,000 $\mu mol \cdot m^{-2}$, preferably between 6,000 and 50,000, and yet more preferably between 12,000 and 45,000 $\mu mol \cdot m^{-2}$, for example. At the final stage of the culture, at a cell density between $10^7$ and $10^8$ cells per ml, the total supply of light per hour may be increased to between 45,000 and 300,000, for example preferably, between 45,000 and 200,000 $\mu mol \cdot m^{-2}$, and for example, yet more preferably, between 50,000 and 150,000 $\mu mol \cdot m^{-2}$.

According to an embodiment of the invention, at the initial stage of the culture (at a cell density between $10^5$ and $5 \times 10^5$ cells per ml), the culture is illuminated with 30 flashes per hour, each flash having a duration of 30 seconds and an intensity between 5 and 10 $\mu mol \cdot m^{-2} \cdot s^{-1}$, which gives a total supply of light per hour of 2,250 $\mu mol \cdot m^{-2}$ to 4,500 $\mu mol \cdot m^{-2}$. Then, at the intermediate stage (at a cell density between $10^6$ and $10^7$ cells per ml), the culture is illuminated with 30 flashes per hour, each flash having a duration of 30 seconds and an intensity between 15 and 50 $\mu mol \cdot m^{-2} \cdot s^{-1}$, which gives a total supply of light per hour of 13,500 to 45,000 $\mu mol \cdot m^{-2}$. Then, at the final stage of the culture (at a cell density between $10^7$ and $10^8$ cells per ml), the culture is illuminated with 30 flashes per hour, each flash having a duration of 30 seconds and an intensity between 50 and 150 $\mu mol \cdot m^{-2} \cdot s^{-1}$, which gives a total supply of light per hour of 45,000 to 135,000 $\mu mol \cdot m^{-2}$.

According to an embodiment of the invention, for example, when the duration of the flashes is for example of less than a minute, or less than a second, at the initial stage of the culture (at a cell density between $10^5$ and $5 \times 10^5$ cells per ml), the culture is illuminated with 30 flashes per hour, each flash having a duration of 10 seconds and an intensity between 50 and 100 $\mu mol \cdot m^{-2} \cdot s^{-1}$, which gives a total supply of light per hour of 15,000 $\mu mol \cdot m^{-2}$ to 30,000 $\mu mol \cdot m^{-2}$. Then at the intermediate stage (at a cell density between $10^6$ and $10^7$ cells per ml), the culture is illuminated with 50 flashes per hour, each flash having a duration of 10 seconds and an intensity between 200 and 300 $\mu mol \cdot m^{-2} \cdot s^{-1}$, which gives a total supply of light per hour of 100,000 to 150,000 $\mu mol \cdot m^{-2}$. Then, at the final stage of the culture (at a cell density between $10^7$ and $10^8$ cells per ml), the culture is illuminated with 120 flashes per hour, each flash having a duration of 10 seconds and an intensity between 350 and 450 $\mu mol \cdot m^{-2} \cdot s^{-1}$, which gives a total supply of light per hour of 420,000 to 540,000 $\mu mol \cdot m^{-2}$.

The light supply to the cultures may be obtained by lamps distributed around the external wall of the fermenters. A clock triggers these lamps for defined illumination times.

The fermenters are preferentially located in an enclosure, shielded from daylight, whose ambient temperature may be controlled.

As the applicant could ascertain, the fact that the thus selected strains have good growth capabilities in mixotrophic mode, in the presence of discontinuous and/or variable light, predisposes said strains to a higher production of polyunsaturated fatty acids, notably DHA and/or EPA and/or a higher production of one or more carotenoid(s), more particularly fucoxanthin.

The method of culture according to the invention thus allows selection of strains of the genus *Nitzschia*, in particular of the species *Nitzschia brevirostris*, with mixotrophic character, similar to that isolated by the applicant and deposited at the CCAP under the accession number CCAP 1052/21, and having a high yield of polyunsaturated fatty acids and/or carotenoid(s). This method of culture is characterized in that it comprises the following steps:

a) culture, in mixotrophic mode, of one or more strains of the genus *Nitzschia*, under conditions of illumination that is discontinuous and/or variable over time, the illumination having variations in intensity, the amplitude of which is comprised between 5 $\mu mol \cdot m^{-2} \cdot s^{-1}$ and 1,000, preferably between 5 and 400 $\mu mol \cdot m^{-2} \cdot s^{-1}$, these variations taking place between 2 and 3,600, preferably 5-400 times per hour, b) a step of maintaining said culture over several generations, in the presence of an organic carbon-containing substrate in the culture medium, and optionally c) a step of recovery of the thus cultured microalgae.

By "step of recovery", it is meant more particularly the isolation of the strain or strains for which the number of cells increased the most during said generations.

Advantageously, culture in mixotrophic mode is carried out under conditions of illumination that is discontinuous and/or variable over time, the illumination having variations in intensity, the amplitude of which is comprised between 5 $\mu mol \cdot m^{-2} \cdot s^{-1}$ and 400 $\mu mol \cdot m^{-2} \cdot s^{-1}$, these variations taking place between 2 and 200 times per hour.

For carrying out selection of the strains, different strains of the genus *Nitzschia*, in particular of the species *Nitzschia brevirostris*, may be cultured, in parallel, on microplates in one and the same enclosure, with precise monitoring of the conditions and evolution of the different cultures. It is, thus, easy to determine the response of the different strains to discontinuous and/or variable illumination and, if applicable, to the addition of one or more organic carbon-containing substrates to the culture medium. The strains that respond favourably to the discontinuous and/or variable illumination and to the organic carbon-containing substrates, generally provide a better yield for the production of carotenoids and lipids in terms of quality (polyunsaturated fatty acids more abundant in the lipid profile and fucoxanthin more abundant among the carotenoids) and in terms of quantity (the lipids contain a higher proportion of DHA and/or EPA).

The microalgae may be selected in a fermenter from a heterogeneous population, and from which one aims to select the variants favoured by the manner of selection according to the invention, combining discontinuous and/or variable light, having a specific range of light intensity and a specific frequency, with mixotrophic culture conditions. In this case, culture is carried out by maintaining the microalgae in cultures over many generations, and then an isolation of the components that have become predominant in the culture medium, is performed at the end of culture.

The method of culture according to the invention also makes it possible to produce lipids.

In this case, the method according to the invention further comprises the following steps:

d) a step of recovery of the lipids from the microalgae, and optionally e) the extraction of the DHA and/or the EPA from the recovered lipids.

The method of culture according to the invention also makes it possible to produce carotenoids.

In this case, the method according to the invention further comprises the following steps:

d) a step of recovery of the hydrophobic matter from the microalgae, and optionally e) the extraction of the DHA and/or the EPA and/or the fucoxanthin from the hydrophobic matter recovered.

The method of culture according to the invention may also be applied to any species of the genus *Nitzschia*, capable of growing under the mixotrophic conditions according to the invention, and capable of producing DHA and/or EPA and/or fucoxanthin.

The method of culture according to the invention makes it possible to optimize the production of the biomass obtained from the culture. It also makes it possible to enrich the thus cultured microalgae in polyunsaturated fatty acids, more particularly in DHA and/or EPA, and/or enrich the microalgae thus cultured in carotenoid(s), more particularly in fucoxanthin.

Therefore, the invention is also directed to optimizing the production of biomass, as well as the production of lipids, notably of fatty acids, through the culture of microalgae of the genus *Nitzschia* with mixotrophic character, preferably cultured or selected according to the methods mentioned above, then the recovery of the thus cultured microalgae in order to extract the lipids therefrom, in particular DHA and/or EPA. The invention is also directed to optimizing the production of carotenoid(s), more particularly of fucoxanthin. The strains of the species *Nitzschia brevirostris* are especially concerned.

The methods for selectively extracting the lipids, including EPA and ARA, are known to one skilled in the art and are, for example, described by [Bligh, E. G. and Dyer, O. K. (1959); A rapid method of total lipid extraction and purification, Can. J. Biochem. Physiol., 37:911-917] and by [McCreary D K, Kossa W C, Ramachandran S, Kurtz R R. (1978), "A novel and rapid method for the preparation of methyl esters for gas chromatography: application to the determination of the fatty acids of edible fats and oils", J Chromatogr Sci. 16(8):329-31.]

The methods of extraction and analysis of the carotenoids, including fucoxanthin, are known to one skilled in the art and are, for example, described by Wright et al. (1991) (S. W. Wright, S. W. Jeffrey, R. F. C. Mantoura, C. A. Llewellyn, T. Bjornland, D. Repeta, N. Welschmeyer: Improved HPLC method for the analysis of chlorophylls and carotenoids from marine phytoplankton. Marine ecology progress series: Vol. 77: 183-196, 1991).

The invention also relates to the microalgae of the genus *Nitzschia*, which can be obtained according to the method of the invention as previously described. These microalgae are enriched in polyunsaturated fatty acids. The total lipids of such microalgae generally comprise more than 20%, often more than 25% and sometimes even more than 30% of DHA and/or EPA with respect to the total percentage of lipids. The microalgae can also comprise a fucoxanthin content of more than 0.2% of dry matter, preferably more than 0.25% of dry matter of the microalgal dry matter.

EXAMPLE 1

The cultures of *Nitzschia brevirostris* FCC 810 were carried out in 2 L usable capacity fermenters (bioreactors)

with dedicated automatic controllers with computerized supervision. The pH of the system is adjusted by adding base (a 1N sodium hydroxide solution) and/or acid (a 1N sulphuric acid solution). The culture temperature is set to 25° C. Stirring is achieved using 2 stirring rotors mounted on the shaft according to the Rushton configuration: three-blade impellers with downward pumping. The stirring speed and the air flow rate are regulated to a minimum=100 rpm and to a maximum=250 rpm and Qmin=0.5 vvm/Qmax=2 vvm respectively. The bioreactor is equipped with an external lighting system surrounding the transparent tank.

The reactors are inoculated with a preculture prepared on a stirring table (140 rpm) in a controlled-temperature enclosure (25° C.) and illuminated between 80 and 100 µE. Pre-cultures and cultures in bioreactors are carried out in the F medium plus silica enriched with nitrogen. The organic carbon-containing substrate used for the mixotrophic culture in a bioreactor is glucose at concentrations between 100 mM and 150 mM.

Monitoring of the Cultures:

The total biomass concentration is monitored by measuring the dry mass (filtration on a Whatman GFB filter, then oven drying, at 100° C. for a minimum of 24 h before weighing).

Regarding the quantification of the total lipids, $7 \cdot 10^8$ cells/mL were extracted. Methods for extracting lipids are known to one skilled in the art.

Illumination:

The culture is illuminated with 180 flashes per hour, each flash having a duration of 5 seconds and an intensity of 300 $\mu mol \cdot m^{-2} \cdot 1$.

The light supply to the cultures in the bioreactor was obtained by LED (light-emitting diode) lamps distributed around the external wall of the fermenter. The power supply to the LEDs is triggered by automated control for the illumination time or the flashes.

Results:

|  | Dry mass (g/L) | Total lipids (% of dry mass) | % DHA | % EPA | Fucoxanthin (mg/g) |
|---|---|---|---|---|---|
| Mixotrophy with flashes | 35.1 +/− 0.7 | 23.6 +/− 0.4 | 0.6 +/− 0.5 | 26 +/− 1 | 2.2 +/− 0.1 |
| Heterotrophy | 25.4 +/− 0.2 | 24 +/− 0.3 | 0.8 +/− 0.4 | 22 +/− 1 | 0.8 +/− 0.1 |

The invention claimed is:

1. A method for increasing the production of lipids and carotenoids in a culture of microalgae of the genus *Nitzschia*, comprising the following step:

a) culturing, in mixotrophic mode, of one or more strains of microalga of the genus *Nitzschia*, over several generations in a culture medium comprising a carbon-containing substrate selected from the group consisting of lactate, lactose, saccharose, acetate, glycerol, glucose, cellulose derivatives and mixtures thereof, under conditions of alternation of illuminated phases and phases of darkness, wherein illumination is provided in the form of flashes of light, said flashes having a duration of between 5 seconds and 10 minutes, with an intensity—between 5 and 1,000 $\mu mol \cdot m^{-2} \cdot s^{-1}$, said flashes occurring between 2 and 3,600 times per hour, and wherein the phases of darkness occupy more than half of the time during which the microalgae are cultured; and b) recovering the cultured *Nitzschia* microalgae, the microalgae being charged with said lipids and carotenoids.

2. The method according to claim 1, wherein the microalga is from the species *Nitzschia brevirostris*.

3. The method according to claim 2, wherein said microalga of the species *Nitzschia brevirostris* corresponds to the strain FCC 810, deposited with the CCAP (Culture Collection of Algae and Protozoa), under the accession number CCAP 1052/21.

4. The method according to claim 1, wherein the organic carbon-containing substrate in the culture-medium is at a concentration from 5 mM to 1 M, or from 50 mM to 800 mM, or from 70 mM to 600 mM, or from 100 mM to 500 mM.

5. The method according to claim 4, wherein said organic carbon-containing substrate is glucose, and the glucose is present at a concentration of at least 50 mM.

6. The method according to claim 1, wherein said flashes of light have a duration of between 10 seconds and 2 minutes, or between 20 seconds and 1 minute.

7. The method according to claim 1, wherein the number of flashes of light is between 10 and 150, or between 15 and 100, or between 20 and 50 times per hour.

8. The method according to claim 1, wherein the total amount of light in the illumination per hour in micromoles of photons is between 2,000 to 600,000, or between 2,000 to 200,000 $\mu mol \cdot m^{-2}$.

9. The method according to claim 1, further comprising:

c) recovering hydrophobic matter from the recovered microalgae.

* * * * *